United States Patent [19]

Unterleitner

[11] 3,999,856
[45] Dec. 28, 1976

[54] DIFFRACTOMETRIC REFRACTOMETER

[75] Inventor: Fred C. Unterleitner, Palo Alto, Calif.

[73] Assignee: Monsanto Research Corporation, St. Louis, Mo.

[22] Filed: Jan. 2, 1976

[21] Appl. No.: 646,294

[52] U.S. Cl. .............................. 356/107; 356/111; 356/130; 356/246
[51] Int. Cl.² ......................................... G01B 9/02
[58] Field of Search .......... 356/107, 111, 130, 246

[56] References Cited
UNITED STATES PATENTS

| | | | |
|---|---|---|---|
| 2,703,033 | 3/1955 | Svensson | 356/107 |
| 2,745,310 | 5/1956 | Horn | 356/111 |

FOREIGN PATENTS OR APPLICATIONS

| | | | |
|---|---|---|---|
| 38,222 | 4/1965 | Germany | 356/107 |

*Primary Examiner*—John K. Corbin
*Assistant Examiner*—Richard A. Rosenberger
*Attorney, Agent, or Firm*—Bruce Stevens

[57] ABSTRACT

A device useful as a detector for fluid (liquid or gas) chromatograph effluent comprising a light source, a cell divided into sample and reference fluid compartments separated by an opaque diaphragm sufficiently thin to form a Fraunhofer diffraction pattern, means to introduce and remove sample and reference fluids to and from said compartments, means to collimate light from said light source at said diaphragm and through the compartments of said cell, photodetector means capable of sensing phase shift of said diffraction pattern, and means to focus light exiting said compartments on said photodetector. When used as a detector for chromatograph effluent the sample compartment should have a volume less than the smallest volume of eluted fractions from the chromatograph with which the device is used. An especially significant and novel feature of the device is the cell used in the refractometer.

6 Claims, 9 Drawing Figures

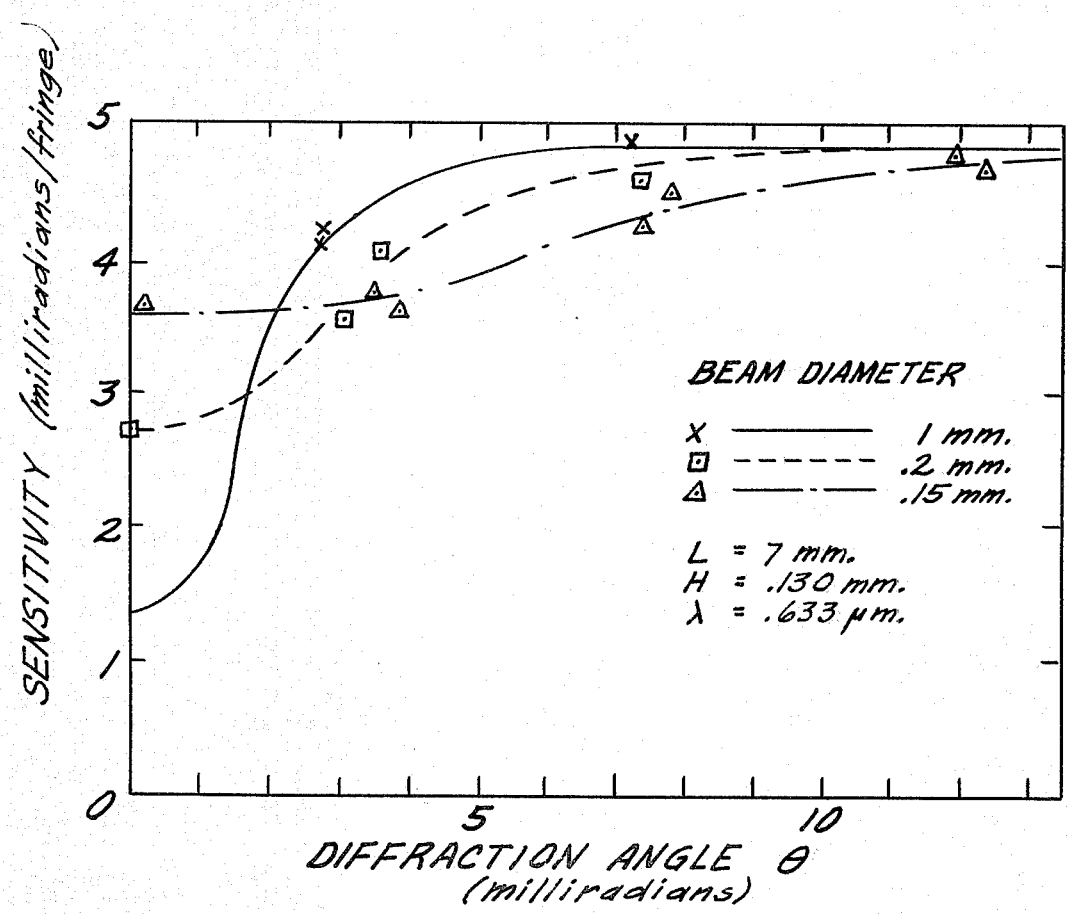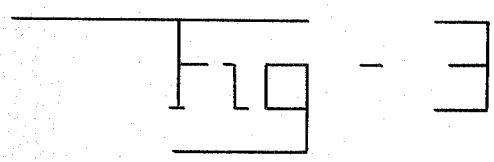

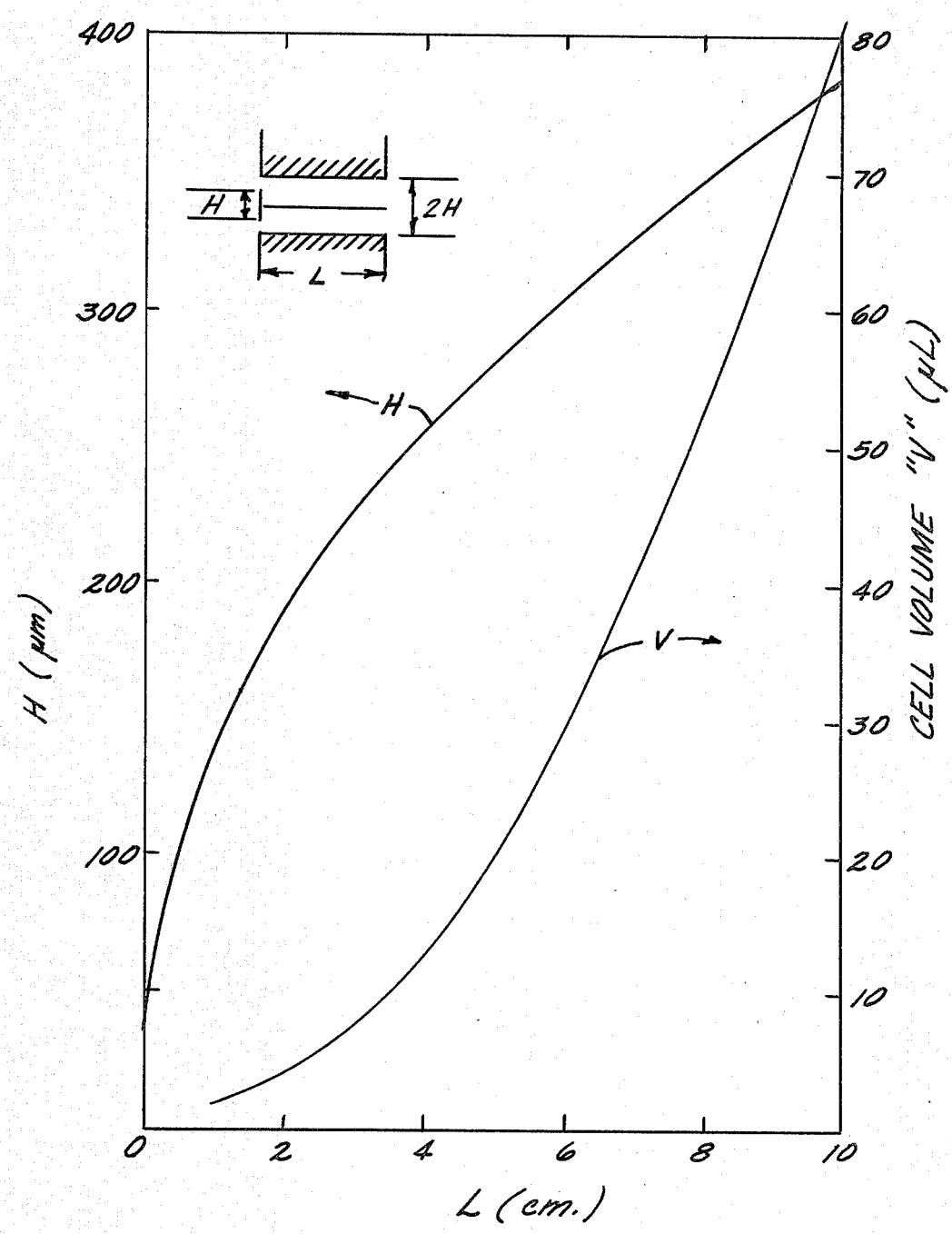
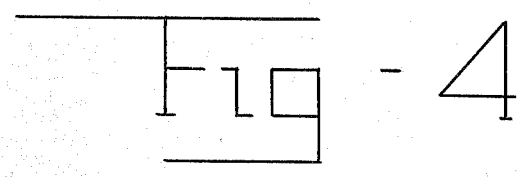

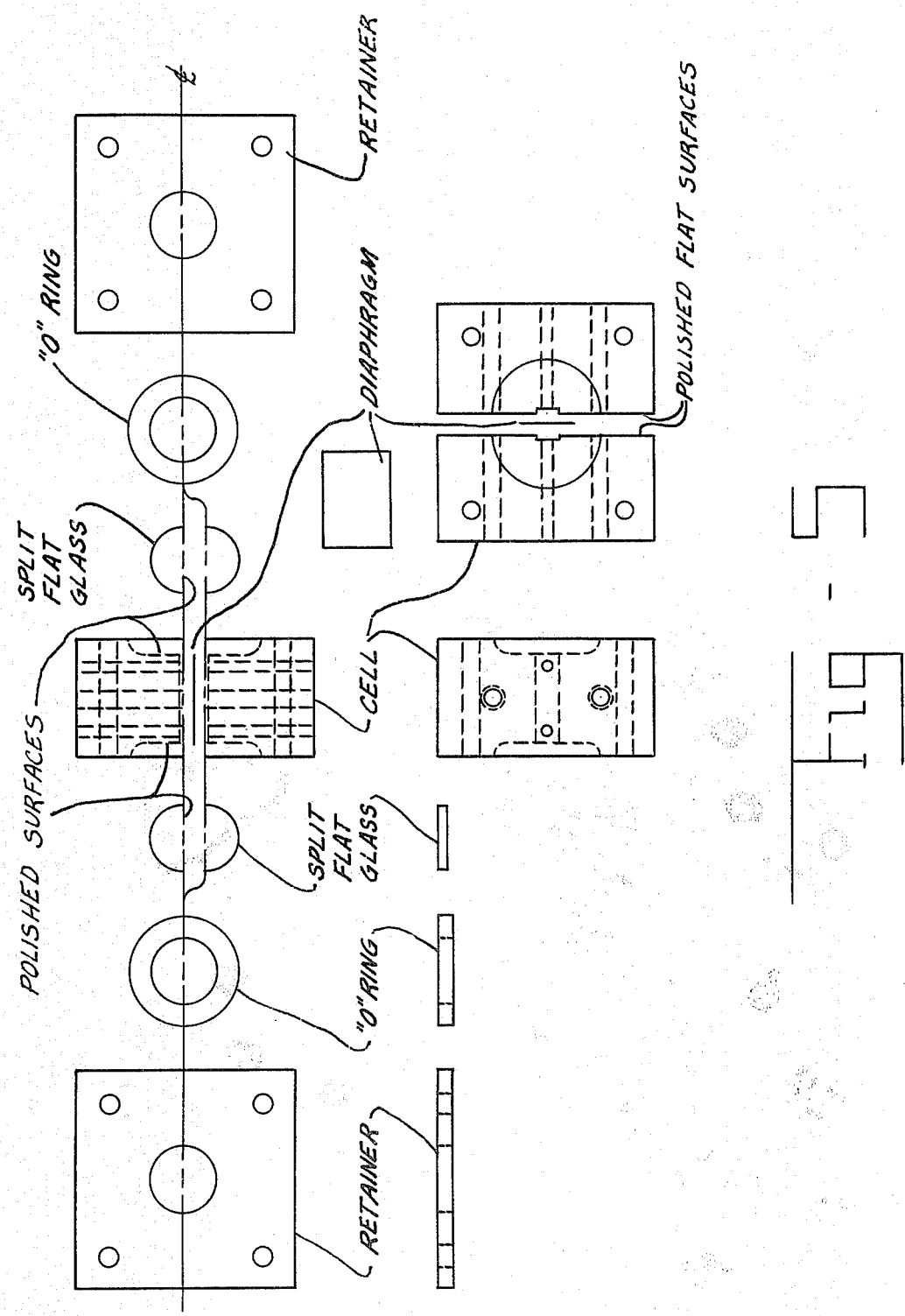

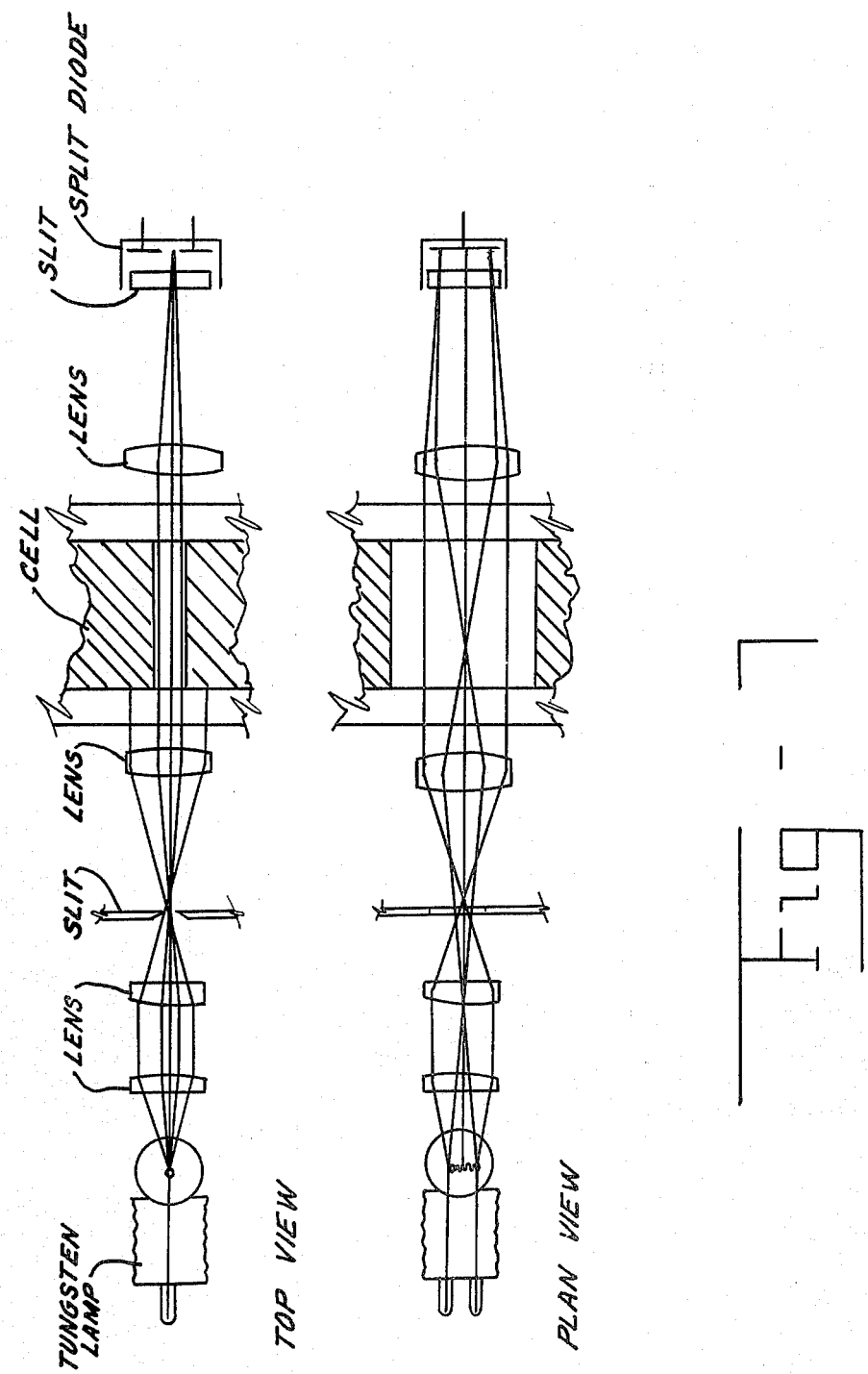

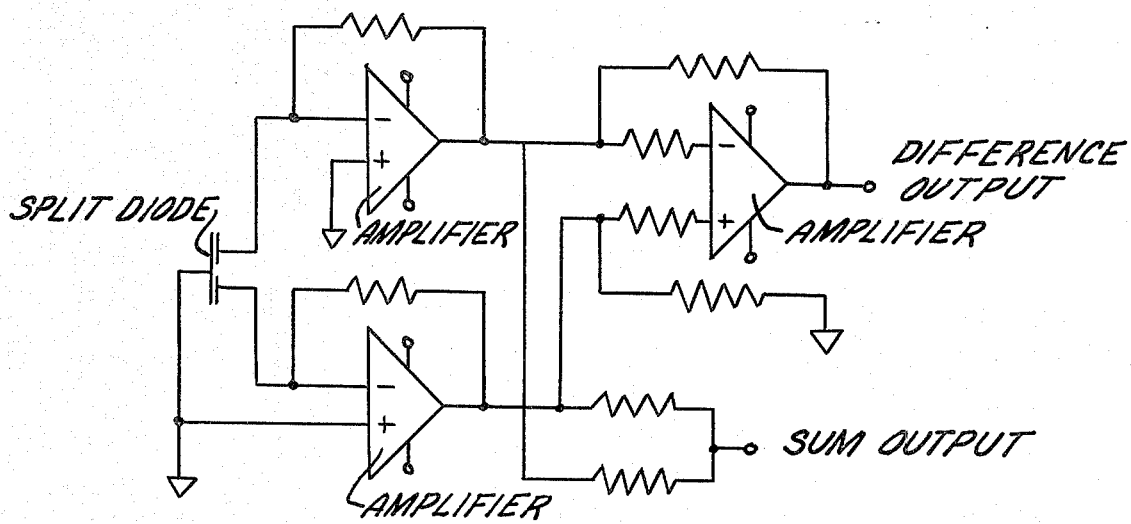
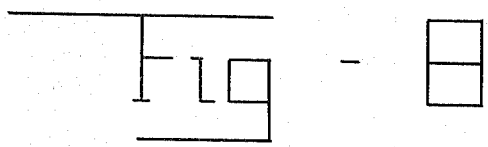

DIFFRACTOMETRIC REFRACTOMETER

BACKGROUND OF THE INVENTION

1. Field of the Invention

Diffractometric refractometers and a novel sample and reference cells usable in the refractometers.

2. Description of the Prior Art

U.S. Pat. No. 2,795,991 teaches an interferometer for indicating the composition of gases based on changes in refractive index including use of a comparative known reference gas.

U.S. Pat. No. 3,035,482 teaches interferometers which are employed for that type of measuring purposes in which the displacement of the interference fringes is used for determining the change in the value of a measurement, for instance, for determining the concentration of a gas.

U.S. Pat. No. 3,090,279 describes an interferometer using a diffraction grating, and either monochromatic or white light can be used.

U.S. Pat. No. 3,472,598 describes an apparatus for determining the refractive index of light permeable substances providing for measuring a reference substance of known refractive index to compare with the measurement of the unknown substance by observation of interference bands.

U.S. Pat. No. 3,487,227 describes an interferometer apparatus especially suitable for measuring gas purity and having three apertures using a monochromatic light source. Fraunhofer interference pattern is produced by this interferometer.

U.S. Pat. No. 3,612,696 describes a refractometer cell for use in liquid chromatography comprising a housing forming a chamber through which radiation can be transmitted, said chamber adapted to receive a test fluid. A radiation-transparent refracting means is positioned within the chamber. In one embodiment, this refractive means is a spherically shaped element. In another embodiment, the refractive means comprises two spaced elements having concave spherically shaped surfaces facing one another. Use with a chromatographic column in a detector is described.

U.S. Pat. No. 3,680,963 describes a refractometer to measure refractive indices of fluids by optical fringe counting. Interference fringes are created by overlapping two coherent beams of light which have traversed different optical paths. One optical path is through an unknown sample fluid and the other is through a known reference fluid. The fringe pattern shifts in direct relation to differences between the two optical path lengths.

In none of this prior art are described sample and reference cells of the design of the present invention and none of the sample cells is especially suitable because of such small sample volume for use in detectors for gas chromatographs. Thermal conductivity detectors are presently used with gas chromatographs, and the cell and device of the present invention has advantages over the thermal conductivity detectors in providing smaller internal volume sample cells (5–10 $\mu$l or even 2 $\mu$l or less), better sensitivity, can be used with carrier gases which may be corrosive or with corrosive samples, and is potentially simpler and lower cost.

SUMMARY OF THE INVENTION

A device useful as a detector for fluid (liquid and gas) chromatograph effluent comprising a light source, a cell divided into sample and reference fluids compartments separated by an opaque diaphragm sufficiently thin to form a Fraunhofer diffraction pattern, means to introduce and remove sample and reference fluids to and from said compartments, means to collimate light from said light source at said diaphragm and through the compartments of said cell, photodetector means capable of sensing phase shift of said diffraction pattern, and means to focus light exiting said compartments on said photodetector. When used as a detector for chromatograph effluent the sample compartment should have a volume less than the smallest volume of eluted fractions from the chromatograph with which the device is used. An especially significant and novel feature of the device is the cell used in the refractometer. Obviously, the device is also useful as a refractive index detector for other than chromatograph effluent.

BRIEF DESCRIPTION OF THE DRAWINGS

The invention will be more clearly understood from the following detailed description of specific embodiments thereof read in conjunction with the accompanying drawings wherein:

FIG. 3 is a graphical presentation of diffraction angle vs. sensitivity for different beam diameters, FIG. 4 is a graphical presentation of baffle width vs. cell length, FIG. 5 is a drawing of the details of a cell of the invention, FIG. 7 is an optical schematic both top and plan views using a tungsten lamp in a device of the invention, and FIG. 8 is an electronics schematic for a split segment photodiode device of the invention.

DESCRIPTION OF THE PREFERRED EMBODIMENTS

The primary goal of this invention is to provide a simple, low cost, small volume detector which will be more reliable than the widely used thermal conductivity cell. The diffractometric refractometer (DR) cell of the present invention can readily be fabricated of materials which can operate continuously at temperatures above 400° C. Since there need be no oxidizable constituents in the cell, accidental injection of air into the column will not damage the detector. When utilizing low cost laser sources currently available, mean operating time between failures in excess of 10,000 hours can readily be achieved, and other system components can be designed to have even lower failure rates. The expense and inconvenience of repair and recalibration should, therefore, be negligible with such a DR detector system.

Figure 1:
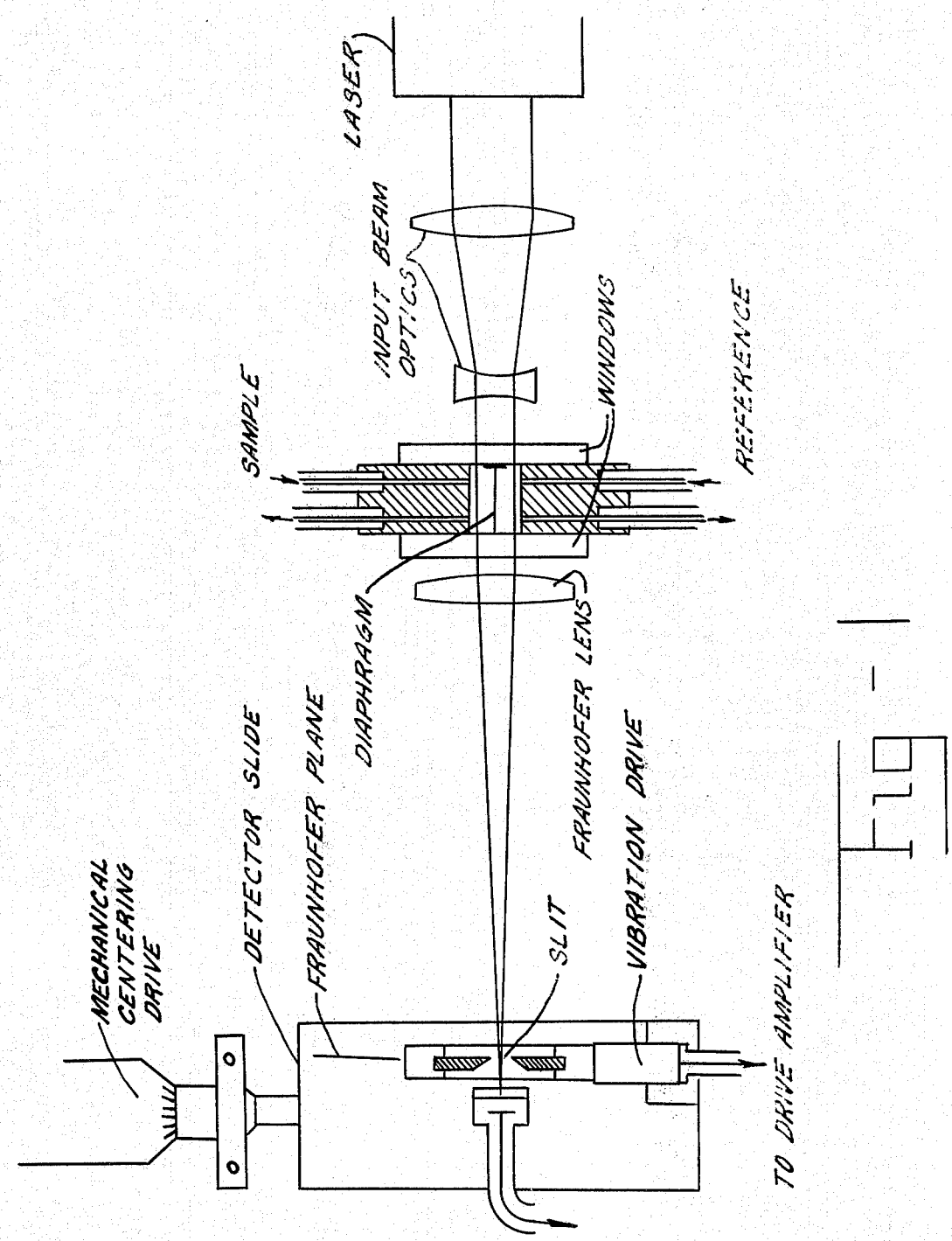
FIG. 1 is a schematic diagram of a device of the invention.

A schematic diagram of a DR detector system is shown in FIG. 1. The basic components are the light source, the cell, the detection slit, the photodetector, and the photocurrent processing electronics. Each of these elements will be discussed in more detail below.

THE DIFFRACTION CELL

Figure 2A:
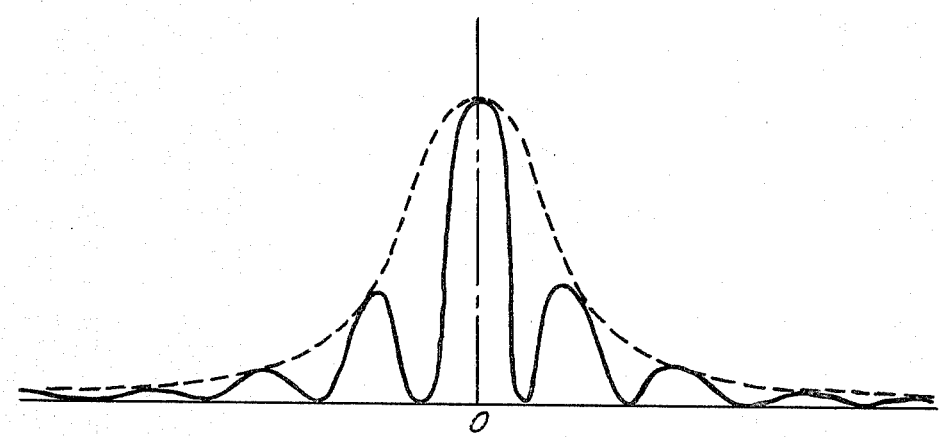
FIG. 2 is two graphical presentations of intensity in the Fraunhofer plane, the first where sample and reference gases are the same and the other where they are different.
Figure 2B:
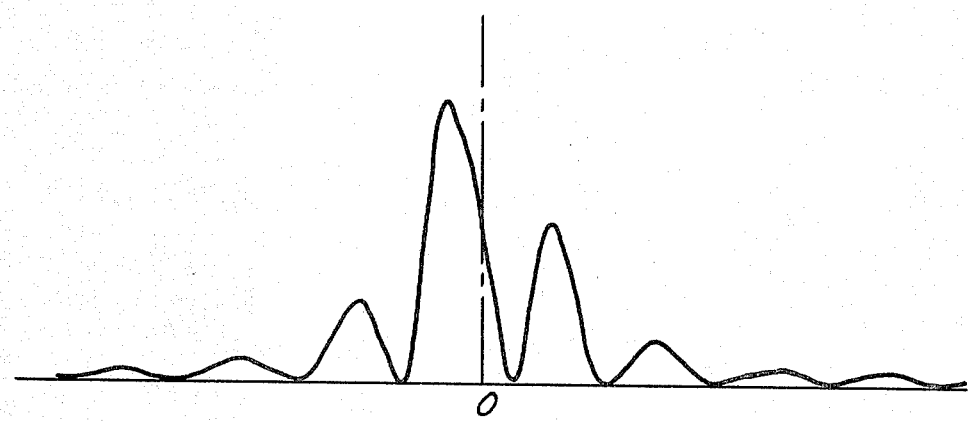

When an opaque plane with a long narrow slit is placed in the path of a light beam, a Fraunhofer diffraction pattern is formed on a distant screen, consisting of uniformly spaced light and dark bands whose spacing is determined by the slit width and the wavelength of the light. If an opaque strip, equal in width to the slit, is placed over the slit and opaque plane is then removed, the diffraction pattern on the distant screen remains the same except for the region where the direct beam strikes the screen. The equivalence of the diffracted intensity for positive and negative diffraction objects having identical geometry is a general law, and we use it as the starting point for the diffractometric refractometer design. If the isotropic media on either side of the opaque strip are identical, the usual symmetrical diffraction pattern is produced in the Fraunhofer plane, as shown in FIG. 2a. If the refractive index of one medium is slightly higher than the other by $\Delta n$ a relative phase shift of $\Delta \phi = 2\pi \, \Delta nL/\lambda$ radians is introduced between the upper and lower sections of the light beam causing the entire pattern to shift in the direction of the higher refractive index (RI) medium, as shown in FIG. 2b. Here L is the path length in the region having differential index and $\lambda$ is the wavelength of the light. By performing the Fraunhofer integration in the presence of small phase shifts, and including the region of the "direct beam", a plot of fringe shift per RI increment (the "sensitivity") as a function of position in the Fraunhofer plane can be made. Such plots for different beam diameters are shown in FIG. 3. By judicious selection of beam diameter, the sensitivity at the center of the pattern can be made almost as high as in the wings. Operation in the "direct beam" results in greater optical signal into the detector and, in general, better signal to noise ratios, particularly with non-laser light sources.

The length of the cell is an important parameter. The Fresnel diffraction in the near field of the leading edge of the diaphragm results in reflection from the face of the diaphragm, which interferes with the diffracted wave at small angles. To avoid this spurious interference, it may be desirable to place a thin opaque strip on the entrance window, which is sufficiently wide to reduce the diffracted light intensity which is incident upon the diaphragm surface to a negligible value. The geometrical arrangement is shown in the inset of FIG. 4, and the relation between the width of the strip and the length of the diaphragm is shown for the case where the diffracted intensity at the far edge of the diaphragm is about 1% of the direct beam intensity. It is clear from this relationship that as the cell length increases, the beam diameter must also increase, so that the active cell volume increases. Under these conditions, the sample cell volume is approximately $V_s = 4\pi\lambda L^2$, where $\lambda$ is the mean wavelength of the beam and L is the length of the cell. The optimum length of the cell is that length which has a sample volume somewhat smaller than the smallest volume of the eluted fractions from the particular chromatographic system being used. The sensitivity of the detector to RI changes increases as $\sqrt{L}$, so the longest cell, consistent with the maximum sample volume for the system, should be used.

For example, cell compartments design to couple efficiently to a Meret FIP 307 gallium arsenide laser might have the following dimensions: 1 cm long (light path) by 0.041 cm wide (both compartments) and 0.318 cm high having a 0.004 cm wide diaphragm separating the sample and reference gas compartments.

FIG. 5 shows the construction of a cell of the invention. A pair of stainless steel blocks each containing a channel through the blocks together with the steel diaphragm when fitted together form the sample and reference compartments of the cell, two holes are provided through each steel block communicating with the channel therein to serve as passages for introducing or removing either sample gas or reference gas, and two bolt holes are provided through each block parallel to the channel for use in assembling the cell. A pair of split glass plates at each end of the blocks fit in recesses in the blocks, sandwich the diaphragm between a pair at each end, and serve as closures for the ends of the compartments. O-rings fit in each recess around the split glass plates to seal the ends of the cell. Retainer plates are provided each with a hole in the center to provide a path for the passage of light through the cell compartments and with bolt holes for assembly of the cell. FIG. 5 shows all parts slightly separated and unassembled for better understanding of the cell construction. It should be noted that unlike the diaphragms of FIGS. 1 and 4 no opaque strip or baffle is provided on the forward edge of the diaphragm to reduce interference since this interference may not be sufficient to bother with as a practical matter.

THE LIGHT SOURCE

A low power (~1.0 mw) HeNe laser would be a suitable source for a practical instrument. For a more compact system a gallium arsenide semiconductor laser or an incandescent lamp operated with a suitable aperture slit are desirable.

Currently available GaAs semiconductor lasers are about 1/10th the cost of the HeNe gas laser, but must be operated in short pulse mode. This is not a severe restriction since the pulse repetition rate can be quite high, and can be synchronized with the slit vibration drive, if necessary. The emitting area of the diode is a narrow slit, which should be aligned parallel to the diaphragm plane to insure adequate spatial coherence. The slightly longer wavelength of 0.90 $\mu$m (compared to 0.63 $\mu$m of the HeNe laser) will not significantly influence performance, aside from requiring slightly larger cell volume for the same length. A minor disadvantage in initial alignment is the non-visibility of the radiation, requiring adjustment by observing silicon detector response, perhaps using an image converter for the initial coarse alignment.

The tungsten (or other non-laser) source has much lower brightness. To provide adequate spatial coherence approaching that of the HeNe laser, but utilizing the entire spectral band from 0.6 $\mu$m to 1.0 $\mu$m, a tungsten source with a circular aperture can provide only $5 \times 10^{-8}$ watts compared to $10^{-3}$ watts for the laser. If a slit source is used, this could be increased to about $10^{-6}$ watts, but cell volume would have to be increased also to pass the wider beam. An input optical power of $10^{-6}$ watts will be adequate to approach the fluctuation noise limited performance of the laser system.

Since the tungsten lamp has a much lower brightness than the other sources, some care must be exercised to couple it efficiently to the cell. The highly incoherent nature of the light emission from non-laser light sources resulted in the development of the theory of partial coherence, so that the diffraction and interference characteristics of optical instruments working with such light sources could be understood and predicted. With such sources, the spatial coherence of light falling on a given area can only be increased at the expense of reduced angular size of the light source. Roughly speaking, coherence is maintained only over an area which falls well within the central diffraction maximum of an incoherently illuminated aperture corresponding to the source size. Therefore, the tungsten lamp is imaged onto a slit, the light from which is then collimated and passed through the cell, as shown in FIG. 7.

The lower light level available with the tungsten lamp source would make it difficult to detect the audio frequency modulation of the vibrating slit. Since photon noise and detection system instabilities do not appear to be limiting factors even in this case, simple D.C. differential sensing of the photocurrents in two detector segments can be utilized. The detector segment gap is about 0.1 mm, so the diffraction pattern at the detector must be large enough that the central maximum for the symmetrical case is at least 2 or 3 times the gap width. This requires that the Fraunhofer plane be at least 100 mm from the cell. A 105 mm F.L. achromatic lens is used to focus the diffraction pattern on the detector plane. An auxiliary slit is placed in front of the detector, having about the width of the primary maximum, to eliminate the effect of subsidiary maxima on the detector output, since the detector segments are much wider than the central peak. When the optical system is properly adjusted, the diffracted intensity drops off rapidly enough for subsidiary maxima that it may not prove necessary to include this slit in a simple leak detection module. The alignment of the segment gap of the detector so that it is parallel to the gas cell diaphragm is critical; an error of 0.05 mm over the 2.5 mm sensitive area height (or ~1.2°) can severely degrade the differential response.

DISPLACEMENT DETECTION

Differential refractive index changes in the cells produce a displacement of the diffraction pattern in the Fraunhofer plane, as discussed above. The position of the central maximum for the symmetrical cell configuration is the optimum position for the displacement sensor because the largest excursions of intensity with refractive index occur there, and the temporal coherence requirement is lowest. Two sensing schemes are proposed, and appear to be capable of approximately the same sensitivity. The first method uses a split silicon photodetector with a differential preamplifier. A shift in the diffraction pattern produces an unbalance in the detector which is proportional to the sine of the optical phase difference. A narrow band synchronous detector should be used to avoid D.C. drift effects in the amplifiers and to average fluctuation noise.

Figure 6:
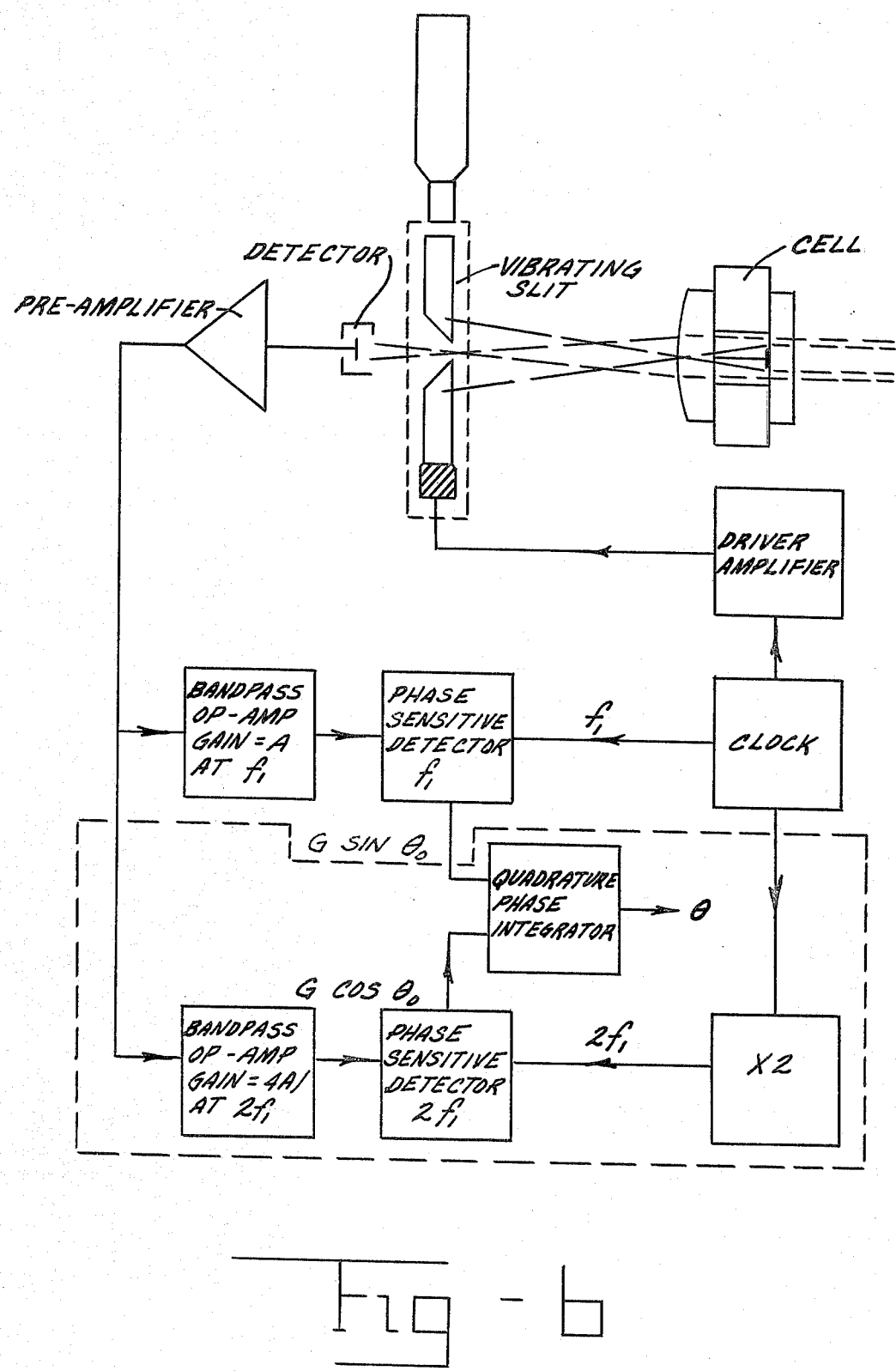
FIG. 6 is a block diagram of the electronics for a vibrating slit type device of the invention.

The second detection scheme uses an oscillating slit in the Fraunhofer plane and a single element fixed photodetector behind it. The light source is either constant or pulsed at a much higher frequency than that of the oscillating slit. A block diagram of such a system is shown in FIG. 6. The photodiode current is A.C. amplified and the component synchronous with the slit frequency is detected. This component is proportional to the sine of the optical phase shift when the slit is at the center of the undeviated pattern. For small displacements, the synchronously detected signal is, therefore, linearly proportional to the refractive index change. Components inside dashed lines of FIG. 6 are needed only if large refractive index differences need to be measured (i.e. $\Delta n > 10^{-5}$ for 1 cm length cell). If larger excusions of refractive index are anticipated, a full quadrature phase detection system can be implemented by also detecting the second harmonic of the slit frequency synchronously. The second harmonic is proportional to the cosine of the optical phase shift, and could be used with a quadrature phase angle integrator to read out linear refractive index difference over a wide dynamic range.

For either detection system, the synchronous detector frequency should be in the medium audio frequency band to minimize low frequency flutter noise introduced by fluid turbulence, both in the cells and in the air paths of the beam outside the cell. While careful design can minimize these turbulence effects, they will tend to be the limiting noise source — particularly with laser light sources. The integration time of the detectors should be of the order of a second or longer for the same reason.

The two segment photodiode detector requires a completely different electronic system. The circuit is shown in FIG. 8. It consists of dual amplifiers feeding a unity gain difference amplifier and a summing output. The output of the difference amplifier is proportional to $\sin \theta$, where $\theta$ is the optical phase angle defined above, while the sum terminal permits monitoring of detector and slit alignment to insure that the detector is properly centered and aligned.

SUMMARY

1. The detector senses optical phase shift due to presence of a high refractivity molecular component in a low refractivity carrier fluid on one side of a thin diaphragm, which serves as a diffraction mask.
2. The sample cell can be made entirely of refractory and chemically inert materials such as stainless steel and fused silica, so that it can be operated at high temperatures and with oxidizing or reducing sample constituents without damage to the cell.
3. The light source is required to have high spatial coherence over the cell aperture, but need not have high temporal coherence (i.e. monochromaticity not required), thus a suitably apertured conventional source can be used as well as a laser.
4. The optical detector system must be sensitive to slight displacements of the diffraction pattern intensity distribution.
5. Mechanical and electronic means for minimizing the effect of low frequency fluctuations in the diffraction pattern due to fluid turbulence and mechanical vibrations should be provided.
6. Reasonable sensitivity can be achieved with active cell volumes as low as 2 $\mu l$, a reduction of several orders of magnitude below those of thermal conductivity detectors.
7. Small cell volume should make practical true differential sensing of peaks at column limited resolution.

Although the invention has been described in terms of specified embodiments which are set forth in considerable detail, it should be understood that this is by way of illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

What is claimed is:

1. A cell suitable for use in a diffractometric refractometer detector comprising sample and reference fluid compartments separated by an opaque diaphragm sufficiently thin to cause formation of a Fraunhofer diffraction pattern when collimated light is focused after passing said diaphragm, means to introduce and remove sample and reference fluids to and from said compartments, the ends of said compartments perpendicular to said diaphragm being transparent to light providing light paths through said compartments parallel to said diaphragm.

2. A cell of claim 1 having a sample compartment with a volume less than the smallest volume of eluted fractions from a chromatographic system with which said cell is to be used.

3. In a device capable of measuring refractive index comprising light source means, a sample fluid compartment and a reference fluid compartment, means to form a Fraunhofer diffraction pattern and photodetector means to receive light transmitted through said compartments and capable of sensing phase shift of said diffraction pattern, the improvement making the device especially useful as a detector for chromatograph effluent comprising a cell divided into sample and reference fluid compartments separated by an opaque diaphragm sufficiently thin to form a Fraunhofer diffraction pattern.

4. A device of claim 3 having a sample compartment with a volume less than the smallest volume of eluted fractions from a chromatograph with which said device is to be used.

5. A device of claim 3 wherein said light source is a tungsten filament lamp, lens means and slit means are positioned between said light source and said cell to collimate light at said diaphragm and through said compartments, a split photodiode, lens means for focusing light leaving said compartments on said diode, and means to detect the output of each side of said diode.

6. A device of claim 3 wherein said light source is a laser, lens means are positioned between said light source and said cell to collimate light at said diaphragm and through said compartments, a vibrating slit positioned in the Fraunhofer plane, a photodiode, lens means to focus light exiting said compartments through said vibrating slit on said photodiode, and means to detect the alternating current components of the output of said photodiode at the vibrating frequency of the slit and at twice the vibrating frequency of the slit.

* * * * *